United States Patent [19]

Khan et al.

[11] Patent Number: 5,688,982

[45] Date of Patent: Nov. 18, 1997

[54] NO-BLEACH PROCESS FOR MAKING SULFONATED FATTY ACID ALKYL ESTER SURFACTANT

[75] Inventors: Vajih A. Khan, Loveland; Michael T. Creedon; Benjamin E. Chapman, both of Cincinnati, all of Ohio

[73] Assignee: The Procter & Gamble Company, Cincinnati, Ohio

[21] Appl. No.: 303,283

[22] Filed: Sep. 8, 1994

Related U.S. Application Data

[63] Continuation of Ser. No. 107,504, Aug. 20, 1993, abandoned.

[51] Int. Cl.$^6$ ............................................. C11D 1/28
[52] U.S. Cl. ........................................ 554/98; 554/97
[58] Field of Search ................................ 554/97, 98

[56] References Cited

U.S. PATENT DOCUMENTS

| | | | |
|---|---|---|---|
| 3,142,691 | 7/1964 | Wulff et al. | 554/96 |
| 3,997,576 | 12/1976 | Oghoshi et al. | 554/98 |
| 4,021,460 | 5/1977 | Oghshi et al. | 260/400 |
| 4,344,889 | 8/1982 | Inchauspe | 554/96 |
| 4,404,143 | 9/1983 | Sekiguchi et al. | 260/400 |
| 4,495,092 | 1/1985 | Schmid et al. | 252/559 |
| 4,547,318 | 10/1985 | Kloetzer et al. | 260/400 |
| 4,552,702 | 11/1985 | Schmid et al. | 260/428 |
| 4,579,687 | 4/1986 | Sekiguchi et al. | 260/400 |
| 4,650,611 | 3/1987 | Schmid | 260/410.9 R |
| 4,668,438 | 5/1987 | Pierr et al. | 260/400 |
| 4,671,900 | 6/1987 | Schmid et al. | 260/400 |
| 4,695,409 | 9/1987 | Piorr et al. | 260/400 |
| 4,820,451 | 4/1989 | Piorr et al. | 260/400 |
| 4,990,288 | 2/1991 | Piorr et al. | 554/97 |

FOREIGN PATENT DOCUMENTS

| | | |
|---|---|---|
| 0 483 413 A1 | 6/1992 | European Pat. Off. . |
| 35 35 184 | 4/1986 | Germany . |
| 40 12 106 A1 | 10/1991 | Germany . |
| 40 17 463 | 12/1991 | Germany . |
| 40 17 468 | 12/1991 | Germany . |
| 40 34 242 | 4/1992 | Germany . |
| 40 35 935 A1 | 5/1992 | Germany . |
| 290842 | 11/1990 | Japan . |
| HEI-3-101828 | 4/1991 | Japan . |

OTHER PUBLICATIONS

α–Sulfonated Fatty Acids and Esters: Manufacturing Process, Properties, and Applications, TECHNICAL, W. Stein & H. Baumann.

Development of α–Sulfo Fatty Acid Esters, World Conference and Exposition on Oil Chemicals, Oct. 7–12, 1990, by Takeo Inagaki.

*Primary Examiner*—Deborah D. Carr
*Attorney, Agent, or Firm*—Ken K. Patel; Jacobus C. Rasser; Jerry J. Yetter

[57] ABSTRACT

An improved, no-bleach process for the production of sulfonated fatty acid alkyl ester surfactants containing sulfonated fatty acid alkyl esters and less than 10% of sulfonated fatty acid disalt, fatty acid salt (soap), and fatty acid alkyl ester impurities, said process comprising sulfonating fatty acid alkyl esters, reacting with a $C_1$ to $C_8$ alcohol, and continuously neutralizing with an alkoxide in a substantially anhydrous medium of a $C_1$ to $C_8$ alcohol, wherein the process does not consist of a

26 Claims, 2 Drawing Sheets

NO-BLEACH PROCESS FOR MAKING SULFONATED FATTY ACID ALKYL ESTER SURFACTANT

This is a continuation of application Ser. No. 08/107,504, filed on Aug. 20, 1993 now abandoned.

TECHNICAL FIELD

This invention relates to a no-bleach process for preparing sulfonated fatty acid alkyl ester surfactants which, following a separate color improvement process, are useful in detergent compositions including laundry detergent compositions.

BACKGROUND OF THE INVENTION

Sulfonated fatty acid alkyl ester surfactants (alternatively referred to as α-sulfo fatty acid alkyl ester surfactants, alkyl ester sulfonate surfactants, etc.) are well-known in the detergent field and have been disclosed in, e.g., U.S. Pat. Nos. 5,118,440 (Cutler et al) and 4,438,025 (Satsuki et al), Japanese Laid Open Patent Publication Number 60-133097 (Application No. Showa 58-240021), Japanese Laid Open Patent Publication Number Sho 63-12466 (Patent Application No. Sho 61-151030), Japanese Laid Open Patent Publication Number Sho 59-105099 (Patent Application No.: Sho 57-215962), Japanese Laid Open Patent Publication Hei 2-173196 (Patent Application No. Sho 63-330479), Japanese Laid Open Patent Publication Number Sho 62-43500 (Patent Application No.: Sho 60-183729), and Japanese Laid Open Patent Publication Number Sho 50-151905 (Patent Application No.: 49-60284). Several processes for the manufacture of these sulfonated fatty acid alkyl ester surfactants have been disclosed in, e.g., U.S. Pat. Nos. 4,695,409 (Piorr et al) and 4,820,451 (Piorr et al), German Patent Application 3 535 184 (Imamura et al), Japanese Laid Open Patent Publication Number 290842/90 (Application Number 113423/89), and "The Journal of the American Oil Chemists Society", Vol. 52 (1975), pp. 323–329.

The processes for making the sulfonated fatty acid alkyl ester surfactants described in the technical literature, though, disclose, during at least one process step, the practicability and desirability of performing such step in aqueous media, e.g., bleaching. The art has recognized certain problems inherent to such process steps, particularly handling difficulties and hydrolysis reactions. Certain of the processes yield undesirable levels of impurities such as sulfonated fatty acids salts (disalt), fatty acid salts (soaps), fatty acid alkyl esters, etc., thereby producing a low-purity sulfonated fatty acid alkyl ester surfactant. These impurities deteriorate the desirable cleaning and viscosity characteristics of the sulfonated fatty acid alkyl ester surfactant. Other impurities are unwanted reaction by-products because of their inherent characteristics. These various impurities are formed via undesirable side reactions which occur during the process for making the sulfonated fatty acid alkyl ester surfactant. Primarily, the side reactions occur in aqueous media.

A process for making a sulfonated fatty acid alkyl ester surfactant having low levels of undesirable impurities has been discovered. The impurities can be eliminated or reduced to acceptable levels by making the sulfonated fatty acid alkyl ester surfactant according to a particular process and carefully controlling certain parameters of the process. Also, by conducting the process steps in non-aqueous media, the reaction mixtures exhibit good handling and in-process flow properties. Therefore, it is an object of this invention to provide a no-bleach process for making sulfonated fatty acid alkyl ester surfactants containing minimal amounts of undesirable impurities. It is a further object of this invention to provide high purity sulfonated fatty acid alkyl ester surfactants having good flow properties during processing and which, following a separate color improvement process, are useful in detergent products.

SUMMARY OF THE INVENTION

The present invention encompasses a novel, no-bleach process for preparing a sulfonated fatty acid alkyl ester surfactant comprising, by weight of the surfactant, from about 90% to 100% of sulfonated fatty acid alkyl esters of the formula:

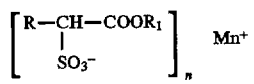

and less than about 10% of impurities selected from the group consisting of sulfonated fatty acid salts, fatty acid salts, fatty acid alkyl esters and mixtures thereof; wherein R is on the average a $C_4$ to $C_{22}$, preferably $C_{10}$ to $C_{16}$ alkyl, $R_1$ is on the average a $C_1$ to $C_8$, preferably $C_1$ to $C_6$, most preferably $C_1$ alkyl, and M is an alkali metal or alkaline earth metal cation, preferably sodium, potassium, lithium, magnesium, or calcium, or a mixture thereof, and n is 1 when M is an alkali metal cation and n is 2 when M is an alkaline earth metal cation; said process comprising:

a) sulfonating fatty acid alkyl esters of the formula:

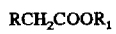

wherein R and $R_1$ are the same as defined above;

b) reacting the product of step a) with from about 3% to 25%, preferably about 10% to 20%, by weight of the product of step a), of a $C_1$ to $C_8$, preferably $C_1$ to $C_6$, most preferably methyl alcohol; and c) continuously neutralizing the product of step b) with an alkoxide of the formula $(R_2O-)_nM^{n+}$ having a concentration of from about 5% to 35%, preferably about 10% to 25%, by weight, in a substantially anhydrous medium of a $C_1$ to $C_8$, preferably $C_1$ to $C_6$, most preferably methyl alcohol; wherein $R_2$ is on the average a $C_1$ to $C_8$, preferably $C_1$ to $C_6$, most preferably $C_1$ alkyl, and M and n are the same as described above; wherein the total amount of alcohol in step c) is from about 30% to 65%, preferably about 30% to 40% by weight, the temperature during step c) is from about 30° to 70° C., preferably about 40° to 60° C., and the pH during step c) is from about 3 to 11, preferably about 6 to 8; and wherein the process does not consist of a bleaching step.

The resultant product solution of the novel process herein may be subjected to a working-up procedure wherein the dark-colored impurities formed during sulfonation of the fatty acid alkyl esters are separated from the resultant solution and, subsequently, the surfactant is recovered from the solution. The surfactant is useful in detergent compositions.

DETAILED DESCRIPTION OF THE INVENTION

Figure 1:
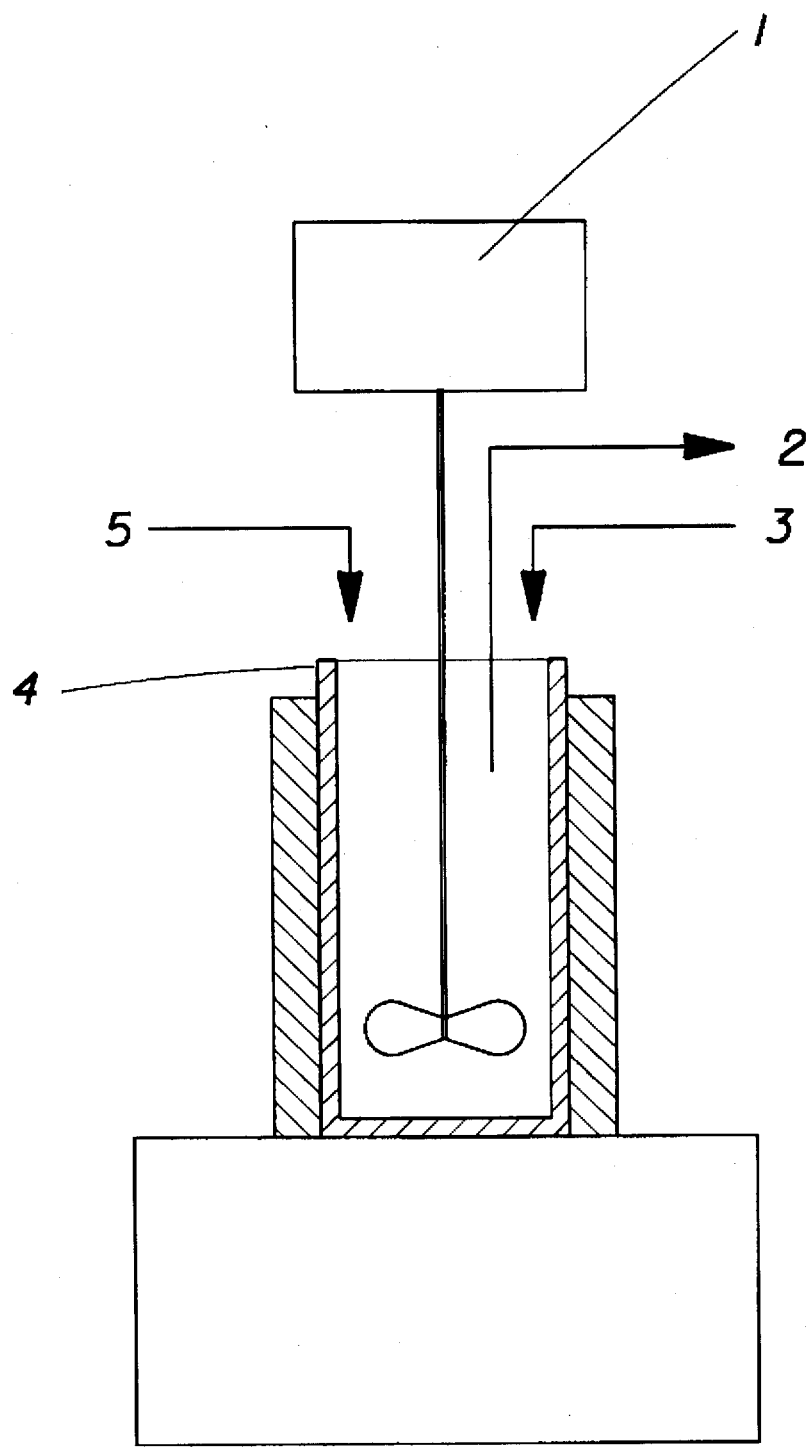

Sulfonated fatty acid alkyl ester surfactants (hereinafter referred to as "the surfactant") are well-known in the art and are disclosed in the technical literature. The surfactant, when prepared according to the process of the present invention, comprises, by weight of the surfactant, from about 90% to 100% of sulfonated fatty acid alkyl esters of the formula:

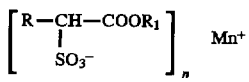

and less than about 10% of of impurities selected from the group consisting of sulfonated fatty acid salts, fatty acid salts, fatty acid alkyl esters, and mixtures thereof; wherein R is on the average a $C_4$ to $C_{22}$ alkyl, $R_1$ is on the average a $C_1$ to $C_8$ alkyl, M is an alkali metal or alkaline earth metal cation, or a mixture thereof, and n is 1 when M is an alkali metal cation and n is 2 when M is an alkaline earth metal cation.

The sulfonated fatty acid alkyl esters (hereinafter referred to as "sulfonated alkyl esters") constitute a major portion of the surfactant. The sulfonated alkyl esters amount to about 90% to 100%, preferably about 95% to 100%, by weight of the surfactant.

The hydrophobic portion of these sulfonated alkyl esters have the sulfonate group at the α position, i.e., the sulfonate group is positioned at the carbon atom adjacent the carbonyl group. The alkyl portion of the hydrophobic portion, which corresponds to the R portion of the sulfonated fatty acid alkyl esters, is on the average a $C_4$ to $C_{22}$ alkyl. Preferably, the alkyl portion of this hydrophobic portion, R, is on the average a saturated straight-chain $C_{10}$ to $C_{16}$ hydrocarbon, particularly when $R_1$ is —$CH_3$.

$R_1$, forming the ester portion of the sulfonated alkyl esters, is a on the average a $C_1$ to $C_8$ alkyl. Preferably, $R_1$ is on the average a $C_1$ to $C_6$ alkyl, and most preferably a $C_1$ alkyl, i.e., methyl.

When considered together, for heavy duty granular laundry detergent compositions, R and $R_1$ preferably contain a total of about 15 to 17 carbons distributed between them. Preferably the distribution is such that R is, on the average, a $C_{14}$ to $C_{16}$ alkyl (approximately a 65% $C_{14}$, 35% $C_{16}$ mix most preferably) and $R_1$ is methyl. For heavy duty liquid laundry and light duty liquid dishwashing detergent compositions, R and $R_1$ preferably contain a total of about 11 to 15 carbons.

The cationic portion, M, is an alkali metal or alkaline earth metal cation or mixture thereof. Preferably, M is selected from the group consisting of sodium, potassium, lithium, magnesium and calcium, and mixtures thereof. Most preferably, M is sodium or a mixture containing sodium. When M is an alkali metal cation (valence=1) n is 1 and when M is an alkaline earth metal cation (valence=2) n is 2.

The impurities contained in the surfactant amount to less than 10%, preferably less than about 5%, by weight of the surfactant. The impurities of importance to the invention hereof are sulfonated fatty acid disalts, fatty acid salts, fatty acid alkyl esters and dimethyl sulfate. These impurities, when present in the surfactant, decrease the desirable cleaning characteristics for detergent compositions (when compared to compositions containing the surfactant without impurities) and worsen handling difficulties during processing of the surfactant.

The sulfonated fatty acid salt impurity comprises, e.g., sulfonated fatty acid salts of the formula:

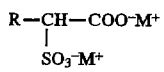

when M is a monovalent cation (n=1). This impurity is commonly referred to as disalt. R is on the average a $C_4$ to $C_{22}$ alkyl, and M is an alkali metal or alkaline earth metal cation with the corresponding n value. It is theorized, although not wishing to be bound by theory, that the the acid form of disalts (di-acids), are formed in the presence of water via two hydrolysis reactions. During sulfonation processes, a portion of the fatty acid alkyl esters react with sulfur trioxide, $SO_3$, to form what is commonly called a mixed anhydride (further explained below). The mixed anhydride reacts with water to form di-acids in one hydrolysis reaction. In the other hydrolysis reaction, un-neutralized sulfonated fatty acid alkyl esters react with water to form di-acids. These di-acids form disalts upon neutralization. Disalt may also form via the direct reaction of the mixed anhydride with a base and water during the neutralization step. The formation of higher levels of disalts have also been observed during batch-type neutralization process steps.

The fatty acid salt impurity (commonly referred to as soaps) comprises fatty acid salts of the formula ($RCH_2COO$—)$_n M^{n+}$. R is on the average a $C_4$ to $C_{22}$ alkyl, M is an alkali metal or alkaline earth metal cation and n is 1 when M is an alkali metal cation and n is 2 when M is an alkaline earth metal cation. Although not wishing to be bound by theory, it is believed that soaps are formed via a hydrolysis reaction wherein un-sulfonated fatty acid alkyl esters react with water to form fatty acids. The fatty acids subsequently form soaps upon neutralization.

The fatty acid alkyl ester impurity comprise fatty acid esters of the formula $RCH_2COOR_1$ wherein R is on the average a $C_4$ to $C_{22}$ alkyl and $R_1$ is on the average a $C_1$ to $C_8$ alkyl. The source of this impurity is believed to be the unreacted (unsulfonated) fatty acid alkyl esters. It is desirable to keep the level of this component as low as possible due to loss of yield, purity, performance and good in-process handleability.

Other impurities which are undesirable may exist as a component of the sulfonated fatty acid alkyl ester surfactant. Di-methyl sulfate ("DMS") having the formula $CH_3$—$OSO_2O$—$CH_3$ is an undesirable component in the surfactant since it is a severe irritant of the eyes, respiratory tract, and skin and can be absorbed into the body through the skin. DMS could be (but is not) particularly problematic in processes of the invention herein because the process steps are conducted in non-aqueous or substantially anhydrous media. It has been observed that processes comprising a step conducted in aqueous media do not result in a surfactant containing DMS.

DMS can be produced during sulfonation of fatty acid methyl esters. Additionally, though, DMS has been observed at higher levels when the neutralization step is conducted in a batch method wherein the base (an alkoxide) is fed into the acid mix (acid form of the sulfonated fatty acid alkyl esters). By conducting the neutralization step c) in a continuous fashion, i.e., the base and acid mixes are simultaneously fed into a reaction bath, the level of DMS observed is significantly reduced. Acceptable DMS impurity levels, i.e, essentially 0%, are provided if the neutralization step c) is conducted in a continuous manner, within the pH and temperature ranges described herein.

In addition to the impurities set forth above, other impurities may be present in the neutralized paste including: sodium methyl sulfate; sodium sulfate; and color bodies.

The color body impurities result from the harsh and complex sulfonation reaction required for alkyl esters, as well as minor side reactions of $SO_3$ with impurities in the alkyl ester starting material (mono-, di- or tri-glycerides for example), or unsaturation in the methyl esters. Even very small quantities of certain light-absorbing chemicals can create a dark visual appearance.

It is important to the production of the sulfonated fatty acid alkyl ester surfactant that the levels of disalt, soap, and fatty acid alkyl ester impurities as well as DMS impurity be kept to a minimum. The reduction in impurity contents in the surfactant improves the performance and formulatability of detergent compositions. The level of these impurities in the end-product, i.e., the surfactant, is minimized by: (1) reacting the product stream of sulfonated fatty acid alkyl ester acid mix with an alcohol and (2) continuously neutralizing the product stream of (1) with an alkoxide in an anhydrous medium.

STARTING MATERIALS

The starting material for the process of this invention include fatty acid alkyl esters of the formula:

$$RCH_2COOR_1$$

wherein R is on the average a $C_4$ to $C_{22}$ alkyl, and $R_1$ is on the average a $C_1$ to $C_8$ alkyl. Normally the alkyl chain, R, is a mixture of alkyl chains ranging in length, on the average, from about 4 carbons to 22 carbons. Preferably R is, on the average, a $C_{10}$ to $C_{16}$ alkyl, and $R_1$ is on the average a $C_1$ to $C_6$ alkyl. $R_1$ is most preferably $C_1$ (methyl) particularly when R is, on the average, a saturated $C_{14}$ to $C_{16}$ hydrocarbon. The R in the fatty acid alkyl ester starting material will correspond to the R for the sulfonated fatty acid alkyl esters in the surfactant since the fatty acid alkyl esters directly react with the reactants in step a) through c) to form the sulfonated alkyl esters.

Preferably the $R_1$ in the fatty acid alkyl ester starting material is the same as the $R_1$ in the sulfonated alkyl ester. To obtain this result, the number of carbon atoms in the alcohol of steps b) and c), the alkoxide in step c) and the $R_1$ of the fatty acid alkyl ester starting material are the same.

The fatty acid alkyl ester starting material can be derived from unbranched $C_6$–$C_{24}$ carboxylic acids and $C_1$–$C_8$ alcohols. From an economic standpoint, the methyl esters of commercial fatty acids are preferred. Methyl esters from palm kernel oil, coconut oil or tallow oil may be used. Since, during the sulfonation step, undesirable color bodies are formed due, in part, to unsaturated chain lengths in the fatty acid alkyl ester, the original fatty acid esters should be hydrogenated to such an extent that their I.V. (iodine value) number is less than about 0.5.

Sulfur trioxide, $SO_3$, which may be used during the sulfonation step a) can be derived from passing a mixture of $SO_2$ and oxygen over a heated catalyst such as platinum or vanadium pentoxide.

The alcohols utilized in the process steps b) and c) are preferably linear primary aliphatic $C_1$ to $C_8$ alcohols. Methanol, the preferred alcohol, can be derived from: (a) high-pressure catalytic synthesis from carbon monoxide and hydrogen, (b) partial oxidation of natural gas hydrocarbons, (c) gasification of wood, peat, and lignite or (d) methane with molybdenum catalyst (experimental). Ethanol can be derived from: (a) ethylene by direct catalytic hydration or with ethyl sulfate as an intermediate, (b) fermentation of biomass, especially agricultural wastes, or (c) enzymatic hydrolysis of cellulose. Propyl alcohol can be derived from the oxidation of natural gas hydrocarbons, also from fusel oil. Butyl alcohol can be derived from the hydrogenation of butyraldehyde, obtained in the Oxo process or condensation of acetaldehyde to form crotonaldehyde, which is then hydrogenated (aldol condensation). Other alcohols can be derived from the hydrogenation of fatty acids.

The alkoxide utilized in the neutralization step c) of the invention is a $C_1$ to $C_8$ alkoxide of the formula $(R_2O—)_nM^{n+}$ and can be derived by dissolving a metal (corresponding to the M in the alkoxide) in an alcohol. Alternatively, the alkoxide can be derived by chemically reacting methanol with a 50% NaOH solution in a column, continuously removing $NaOCH_3$ in methanol solution at the bottom and dilute methanol water solution from the top of the column. See U.S. Pat. No. 2,877,274 (Kramis). Alkoxide in alcohol solutions are also commercially available, e.g., 25% concentration methoxide in methanol commercially available from Occidental Chemical. The alkoxide in alcohol solutions must be substantially anhydrous and, therefore, should not be derived by dissolving, e.g., sodium or potassium hydroxide in a stoichiometric equivalent amount of an alcohol. Such reactions yield one mole of water for every mole of alkoxide produced. In order to obtain the substantially anhydrous conditions required for the alkoxide in alcohol solution of step c), an excess amount of alcohol must be added such that the ratio of unreacted alcohol to water formed by this reaction must be at least about 10:1.

THE PROCESS

Numerous descriptions of processes for the manufacture of the sulfonated fatty acid alkyl ester surfactants are disclosed in the technical literature. The no-bleach process of this invention comprises three essential steps:

a) sulfonating fatty acid alkyl esters, b) reacting with an alcohol, and c) neutralizing with a substantially anhydrous alkoxide solution.

This process results in a high purity sulfonated fatty acid alkyl ester surfactant having good detergency and in-process flow properties. Because the process stream is not subjected to any bleaching step, though, the resultant product solution should be subjected to a color-body removal process before the surfactant is incorporated into a detergent composition.

STEP A—SULFONATION OF THE FATTY ACID ALKYL ESTER

The sulfonation of the fatty acid alkyl esters carried out in step a) of this invention can be carried out by any known sulfonation process. For example, alkyl esters of $C_8$–$C_{20}$ carboxylic acids can be sulfonated with gaseous $SO_3$ in a falling film reactor. The alkyl esters and gaseous $SO_3$ will not completely react to form sulfonated fatty acid alkyl esters at ambient temperatures and pressures. Therefore, this sulfonation process generally includes a mixing step wherein the alkyl esters are brought into contact with a $SO_3$/air mixture (about 5% $SO_3$ in air, by volume) at a molar ratio of $SO_3$:alkyl ester of about 1.1–1.4:1 followed by heating of the mixture to about 75°–95° C. for approximately 20–90 minutes. Preferably, the dew point of the air used for mixing with the $SO_3$ is about −40° C. or lower.

Descriptions of acceptable sulfonation processes are described in "α-Sulfonated Fatty Acids and Esters: Manufacturing Process, Properties, and Applications" by W. Stein and H. Baumann, *The Journal of the American Oil Chemists Society*, Volume 52 (1975), pp 323–325; and U.S. Pat. No.

3,485,856 incorporated herein by reference. See also *Surfactants in Consumer Products*, J. Falbe (Editor), pp. 75–80.

As discussed above, the fatty acid alkyl ester starting material should contain a minimum amount of unsaturated carbon double bonds, i.e., hydrogenated to such an extent that their I.V. number is less than about 0.5. During this sulfonating step color bodies are produced due to the harsh reaction conditions (highly acidic $SO_3$, high temperature, etc.). Regardless of the color quality of the product of step a), this product should not be subjected to any intermediate process step that proceeds in aqueous media, e.g., bleaching. Hydrolysis reactions with intermediate reactants produce the acid form of sulfonated fatty acids which, upon neutralization form the disalt impurity.

It is believed, although not wishing to be bound by theory, that the reaction between the alkyl esters and $SO_3$ in step a) occurs in two stages. First, $SO_3$ reacts with the alkyl ester forming an intermediate complex and activating the carbon at the alpha position (*) as follows:

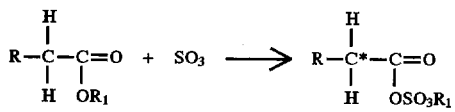

In the second stage, another molecule of $SO_3$ attaches to the activated alpha carbon (*) generating what is commonly referred to as a mixed anhydride:

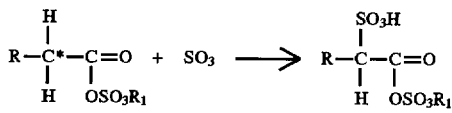

The reaction is best carried out in a falling-film reactor using very dilute $SO_3$ in an inert gas (e.g., 5% $SO_3$ in dry air, by volume). The reaction should be carried out with not more than about 10% to 40% excess $SO_3$ to avoid charring. A significant amount of unreacted fatty acid alkyl ester remains in the product stream leaving the falling film reactor. Therefore, the sulfonating step preferably includes an additional process step wherein the $SO_3$/alkyl ester mix is allowed to react at elevated temperatures (80° to 90° C.), commonly referred to as digestion.

Upon heating in the digestion step, most of the mixed anhydride reacts with fatty acid alkyl esters to form the acid form of sulfonated fatty acid alkyl esters. A significant amount of the mixed anhydride, though, remains after the sulfonation step a).

STEP B—REACTION WITH AN ALCOHOL

The mixed anhydrides, if allowed to react with water, will form sulfonated fatty acids via a hydrolysis reaction. Upon neutralization, these fatty acids form the disalt impurity. The mixed anhydrides may directly react with the alkoxide of step c) to form disalt, too. It is desirable, therefore, to convert the mixed anhydrides remaining in the product stream of step a) to the acid form of sulfonated fatty acid alkyl esters. This is accomplished by reacting the mixed anhydrides with an alcohol. During step b) the anhydride reacts with the alcohol to generate more desired product for neutralization in step c) below, i.e., the acid form of the sulfonated fatty acid alkyl ester, according to the following reaction:

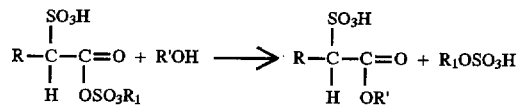

This reaction is relatively fast and most of the remaining mixed anhydrides are converted to the acid form of sulfonated fatty acid alkyl esters when the appropriate level of alcohol is used in step b).

The alcohol of step b) is a $C_1$ to $C_8$ alcohol, preferably a $C_1$ to $C_6$ alcohol, most preferably methanol particularly when the fatty acid alkyl ester starting materials are $C_{14}$–$C_{16}$ fatty acid methyl esters. The product of step a) is reacted with from about 3% to 25%, preferably about 10% to 20%, by weight of the product of step a), of the alcohol.

When determining the level of alcohol to use in step b), one must consider the total amount of alcohol present in step c). Since the alkoxide utilized in step c) is present in an alcohol medium and the total content of alcohol in step c) is from about 30% to 65% by weight, the level of alcohol in step b) and the level of alkoxide in alcohol (the concentration thereof) are closely tied to each other. It is desirable to utilize the alkoxide in alcohol solution at a higher concentration to obtain higher yields of sulfonated fatty acid alkyl ester in the surfactant. Higher yields are also obtained when higher levels of alcohol, within the range of about 3% to 25%, are utilized in step b). Therefore, it is desirable to utilize higher levels of alcohol in step b), i.e., it is preferable to react the product of step a) with from about 10% to 20% of the alcohol. Yet, the concentration of the alkoxide in alcohol must be considered to insure that the total amount of alcohol in step c) does not fall outside of the range of about 30% to 65%. Based on the concentration of alkoxide in alcohol and the stoichiometric amount of alkoxide required to neutralize the product of step b), the alcohol utilized in step b) generally increases when the concentration of alkoxide utilized in step c) increases.

STEP C—NEUTRALIZATION WITH AN ALKOXIDE

The product of step b) is substantially all in the acid form of sulfonated fatty acid alkyl esters in an anhydrous medium of the alcohol of step b). This product of step b) is continuously neutralized with an alkoxide of the formula $(R_2O-)_n M^{n+}$ in a substantially anhydrous medium of $C_1$ to $C_8$ alcohol, wherein $R_2$ is a $C_1$ to $C_8$, preferably $C_1$ to $C_6$, most preferably $C_1$ alkyl; M is an alkali metal or alkaline earth metal cation, preferably sodium, potassium, lithium, magnesium, or calcium, or mixtures thereof; and n is 1 when M is an alkali metal cation and n is 2 when M is a alkaline earth metal cation. To get the maximum conversion rate of the acid form to the salt form of the sulfonated fatty acid alkyl ester, the concentration of alkoxide in alcohol is from about 5% to 35%, preferably about 10% to 25% by weight, and the total amount of alcohol present in the neutralizing step c) is from about 30% to 65%, preferably about 30% to 40% by weight. The amount of alkoxide in alcohol solution utilized in step c) is that amount required to neutralize the product of step b) to obtain a pH of about 3 to 11. When n is 1, the primary reaction taking place during step c) is:

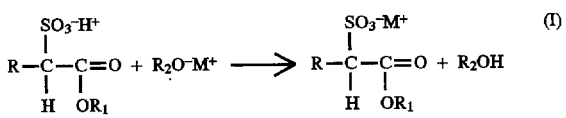

The amount of alkoxide solution required for this reaction is considered to be within the experimental ability of one having ordinary skill in the art.

Reaction I sets forth the neutralization reaction predominantly taking place in step c). It is believed, although not wishing to be bound by theory, that other reactions may also take place during step c), but these are, for the most part, undesirable. Two particularly troublesome reactions which can occur if the process of the invention is not practiced are:

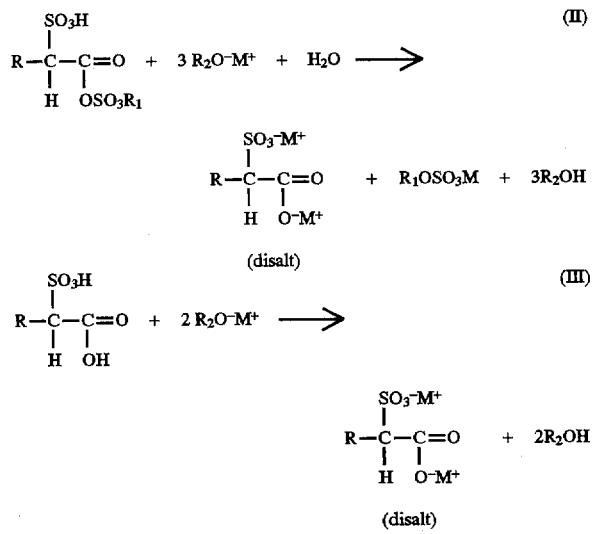

In reaction II, a mixed anhydride reacts with water and alkoxides to produce disalt impurity. In reaction III a sulfonated fatty acid reacts with alkoxides to form disalt impurity. Both reactions, if allowed to occur, produce undesirable disalt impurity in the sulfonated fatty acid alkyl ester surfactant.

Significant amounts of mixed anhydride remain in the flow stream of the process if the product stream of step a) is not reacted with a $C_1$ to $C_8$ alcohol. These mixed anhydrides can react with water and alkoxides in accordance with Reaction II to form the disalt impurity. Furthermore, if these mixed anhydrides are allowed to react with water, such a reaction will produce the acid form of sulfonated fatty acids which, when neutralized, form disalt impurity. Therefore, it is important to both minimize the amount of mixed anhydrides in the feedstock of step c) (i.e., react the mixed anhydrides with an alcohol in accordance with step b)) and minimize the amount of water in step c) (i.e., neutralize the feedstock of step c) in a substantially anhydrous medium).

It is believed that two possible hydrolysis reactions produce the sulfonated fatty acids which subsequently react with alkoxides in accordance with Reaction III to form the undesirable disalt impurity. In the first, the acid form of sulfonated fatty acid alkyl esters react with water to form sulfonated fatty acids. In the second, the mixed anhydrides may react with water to form sulfonated fatty acids. Therefore, it is important in step b) to convert all or nearly all the mixed anhydrides produced in step a) to the acid form of the sulfonated fatty acid alkyl esters. This is accomplished by reacting the product of step a) with the $C_1$ to $C_8$ alcohol in step b). It is also important to run step c) in substantially anhydrous media, i.e., $C_1$ to $C_8$ alcohol media. Any mixed anhydrides present in the process may react with water to form sulfonated fatty acids. Additionally, any acid form of sulfonated fatty acid alkyl esters may react with water to form sulfonated fatty acids. By reacting the product of step a) with a $C_1$ to $C_8$ alcohol and subsequently continuously neutralizing this product with the alkoxide in a substantially anhydrous medium of a $C_1$ to $C_8$ alcohol, a high purity sulfonated fatty acid alkyl ester surfactant is produced comprising less than about 10% of impurities.

As used herein, the term "substantially anhydrous" requires a level of water such that the weight ratio of alcohol to water is at least about 10:1, preferably 30:1. Most preferably the solution is essentially water-free. As discussed above, the presence of water in this process favors undesirable side reactions thereby producing undesirable impurities, e.g., disalt, sulfonated fatty acids, etc. Since one of the reactant streams in step c) is the product stream of step b) and since step c) is conducted in a substantially anhydrous medium, step b) is preferably conducted in a substantially anhydrous medium also. A specific advantage in conducting the process of the invention herein via substantially anhydrous media is the ease of processability of the reactant and product solutions. The technical literature recognizes the problems encountered with sulfonated fatty acid alkyl ester surfactant solutions containing water. It seems that the surfactant forms viscous pastes in water which can require special handling equipment, e.g., special pumps, heat exchangers, etc. An advantage of conducting the process of the invention herein via anhydrous alcoholic media (particularly step c)) is that the process does not require the special equipment that may be required for processes involving an aqueous media. Steps b) and c), conducted in alcoholic media, involve solutions which are relatively fluid and non-viscous which do not require special pumps to process. Additionally, the substantially anhydrous alcoholic medium allows for the effective separation of dark colored impurities during post-neutralization purification steps, i.e., a no-bleach color-body removal process described below.

As used herein, the term "continuously neutralize" means mixing the reactants simultaneously at essentially equimolar ratios in such a manner that intimate mixing of the reactants with vigorous agitation is achieved. It has been observed that normal batch neutralization, wherein an alkoxide solution is added into an acid mix containing the acid form of sulfonated fatty acid methyl esters, produces undesirable levels of DMS (dimethyl sulfate) impurity. Reverse batch neutralization, wherein the acid mix is added into the alkoxide solution, produces undesirable levels of disalt impurity. Continuous neutralization, wherein an acid mix containing the acid form of sulfonated fatty acid alkyl esters and an alkoxide solution are simultaneously fed into a reaction chamber with vigorous agitation, maximizes yield of the surfactant and minimizes impurities including DMS. Sufficient agitation and/or mixing should be provided to allow the reactants to intimately mix and completely react in the chamber. It has been found that a wide range of mixers provide adequate mixing. For example, high shear mixers commercially available from Charles Ross & Son Company, Greerco Company or IKA as well as static motionless mixers (providing shear rates as low as about 5000 $sec^{-1}$) provide the required conditions for continuous neutralization of the reactants. Because the process of the invention herein is conducted in non-aqueous media, i.e., substantially anhydrous alcoholic media, the reactant and product streams exhibit good handling and in-process flow properties. In aqueous media, sulfonated fatty acid alkyl ester surfactants form viscous pastes which are difficult to process. In anhydrous media of a $C_1$ to $C_8$ alcohol, these surfactants are fluid and do not require sophisticated or expensive designs or equipment to process.

The amount of disalt and DMS impurity formed during the process of the invention can be minimized by maintaining the pH of the neutralization step c) between about 3 to about 11, preferably from about 5 to about 9, most preferably from about 6 to 8. pH as referred to in the process of the invention hereof is defined as the pH measured from a 1-2% (by weight of the surfactant) solution of the product of step c) in deionized water with a pH meter.

The temperature during this neutralizing step c) is also important to maximizing surfactant yield and minimizing DMS and is from about 30° to 70° C., preferably from about 40° to 60° C.

The process of the invention herein does not consist of any process step wherein bleaching of the reactants is conducted, i.e., it is a no-bleach process. Such bleaching steps are described in, e.g., U.S. Pat. Nos. 4,695,409 and 4,820,451 which cite references describing acidic bleaching with hydrogen peroxide (U.S. Pat. Nos. 3,142,691; 3,159,547; 3,251,868; and 3,354,187) and hypochlorite (U.S. Pat. No. 3,452,064). Such bleaching steps are generally conducted in aqueous media and would raise the problems discussed above regarding impurities and in-process flow properties. Therefore, the process of the invention does not include any bleaching process step, whether intermediate or in combination with steps a), b), or c). More importantly, the process does not include an aqueous bleaching process step.

A preferred embodiment of the invention herein pertains to a no-bleach process for preparing sulfonated fatty acid methyl ester surfactant. Such process comprises:

a) sulfonating fatty acid methyl esters of the formula:

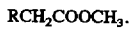

$RCH_2COOCH_3$.

wherein R is on the average a $C_{10}$ to $C_{16}$ alkyl;

b) reacting the product of step a) with from about 5% to 25%, by weight of the product of step a), of a $C_1$ to $C_6$ alcohol, preferably methanol; and c) continuously neutralizing the product of step b) with an alkoxide of the formula $(CH_3O-)_nM^{n+}$ having a concentration of from about 5% to 35% by weight, in a substantially anhydrous medium of a $C_1$ to $C_6$ alcohol, preferably methanol; wherein M is an alkali metal or alkaline earth metal cation, or mixture thereof and n is 1 when M is an alkali metal cation and n is 2 when M is an alkaline earth metal cation;

wherein the total amount of alcohol in step c) is from about 30% to 65% by weight, the temperature during step c) is from about 30° to 70° C., preferably about 40° to 60° C., and the pH during step c) is from about 5 to 9, preferably between about 6 to 8; and wherein the process does not consist of a bleaching step.

This no-bleach process results in high-purity, high-yield surfactant solution containing from about 90% to 100% of sulfonated fatty acid methyl esters (wherein $R_1$ is methyl) and less than about 10% of impurities including disalts, soaps and fatty acid methyl esters. The surfactant solution also contains an acceptable level of DMS impurity. The level of DMS can be minimized, i.e., made essentially 0%, by conducting the process step c) at a temperature between about 40° and 60° C. and at a pH between about 6 and 8.

The resultant product of the process herein is an essentially non-aqueous paste of sulfonated fatty acid alkyl ester surfactant and alcohol. This product may be subjected to a working-up procedure depending on the end use desired. For example, simple separation of the resultant components can be accomplished in many ways including precipitation of the surfactant from the solution, evaporation of the alcohol or a combination thereof.

The known processes for sulfonating fatty acid alkyl esters in accordance with step a) of the invention will likely suffer from the formation of dark-colored impurities. In order to obtain high sulfonation yields, excess sulfonating agent in combination with greater processing times and/or temperatures is required. These conditions can result in undesirable side reactions including the formation of dark-colored impurities.

For aesthetic and other reasons, the dark-colored sulfonated fatty acid alkyl ester compositions are not suitable for use directly in washing or cleansing agents in detergent products. The dark-colored impurities can be separated from the solution comprising the sulfonated fatty acid alkyl ester surfactant and a suitable solvent, e.g., a $C_1$-$C_8$ alcohol, by separation methods described hereinafter. Separation of the dark-colored impurities from the solution can be enhanced with an adsorbent material. After removal of the dark colored impurities, the sulfonated fatty acid alkyl ester surfactant can be recovered from the solvent to yield a product with improved, i.e. lighter, color.

In particular, a process for improving the color of the surfactant (containing dark-colored impurities formed during the preparation of the surfactant) comprises:

(1) forming a solution comprising:
(a) the sulfonated fatty acid alkyl ester surfactant and dark-colored impurities formed during the preparation of the surfactant; and
(b) a solvent in an amount sufficient to substantially dissolve the surfactant;

(2) separating said dark-colored impurities from the solution;

(3) recovering surfactant from the solution.

The step comprising separating dark-colored impurities from the solution of the surfactant in alcohol can be achieved by settling/clarification, centrifugation, filtration, adsorption, or a combination thereof. In a preferred embodiment, the solution is treated with an adsorbent material such as activated carbon, activated alumina, or silica gel.

After separation of the dark-colored impurities from the solution, the surfactant having improved color can be recovered from the solvent solution by known methods. Such recovery methods include, e.g., precipitation of the sulfonated fatty acid alkyl ester from the solution, evaporation of the lower alcohol solvent from the solution or a combination thereof.

The no-bleach process for making sulfonated fatty acid alkyl ester surfactant of the invention hereof is particularly suited to the process for improving the color of the surfactant since the surfactant is already substantially dissolved in a solvent ($C_1$-$C_8$ alcohol). In order to improve the color thereof, one simply needs to separate the dark-colored bodies from the solution and recover the surfactant from the solvent. Having subjected the surfactant to the process for improving the color thereof, i.e., steps (1)–(3) above, the resultant product can be used directly in cleansing and washing agents and products.

As used herein, all percentages, parts, and ratios are by weight unless otherwise stated.

The following examples illustrate the processes of the invention and facilitate its understanding.

EXAMPLE I

The acid form of sulfonated fatty acid methyl esters are produced by conventional sulfonation of palm stearin fatty acid methyl ester. The acid component of the methyl ester consists of saturated fatty acids with an Iodine Value of 0.28 and the following chain length distribution (by weight percent):

$C_{12}$—0.2
$C_{14}$—1.5
$C_{16}$—65.4
$C_{18}$—32.2
$C_{20}$—0.7

R for the methyl ester starting material, therefore, is on the average 14.6. $R_1$ is methyl. The sulfonation reaction is carried out at about 40° C. in an annular falling film reactor (Chemithon Corporation, Seattle, Wash.) using a mixture of sulfur trioxide and air ($SO_3$ content: 5% by volume; $SO_3$ excess: 25% mole percent). The sulfonated methyl ester acid mix is then digested in a closed vessel, e.g., a jacketed plug flow reactor, for 35 to 40 minutes at a temperature of 80° C. to 90° C. The degree of sulfonation after digestion is about 93%. The acid mix for Sample 1D is additionally reacted with 10% methanol (by weight) in a recirculation loop having a residence time of 8 minutes at 75° C. and then is allowed to further react for 18 minutes in a jacketed plug flow reactor at 75° C.

Five separate samples of the acid mix are subsequently neutralized according to four different methods:

Sample 1A—Batch reaction; base into acid. Sample 1A acid mix is neutralized in a batch neutralization process step wherein a basic $NaOCH_3$/methanol solution is added into the acid mix. The reaction is run in a 500 ml 3 neck flask with a mechanically driven paddle stirred, operated at 300 to 500 rpm. The flask is immersed in a stirred water bath maintained at 40° C. To the flask, 150 grams of digested acid is added. A 25% $NaOCH_3$/methanol solution is added with an addition funnel at a rate that keeps the reaction temperature between 45° C. and 50° C. Approximately 55 g of 25% $NaOCH_3$/methanol solution is added to obtain a pH of 7. The flask is kept sealed during the neutralization step except to remove samples to test the pH.

Sample 1B—Batch reaction; acid into base. Sample 1B acid mix is neutralized in a batch neutralization process step wherein the acid mix is added into the basic $NaOCH_3$/methanol solution, commonly referred to as reverse batch neutralization. A basic solution of $NaOCH_3$/methanol solution is prepared by blending 360 ml of a 25% $NaOCH_3$ in methanol solution and 200 ml of methanol (resulting in a $NaOCH_3$/methanol solution at 17.1% w/w concentration). The acid mix is slowly added to the $NaOCH_3$/methanol solution in a one liter vessel under high shear mixing using a Ross model ME 100 high shear mixer operating at about 300–400 rpm, wherein the temperature is maintained at approximately 140° F. The pH of the solution in the vessel is periodically monitored until the solution is at a neutral pH of 7. About 480 grams of acid mix is required for the neutralization to be complete.

Sample 1C—Batch reaction; acid into base. Sample 1C is neutralized in a second 'reverse' batch neutralization process step using the same procedure as in the Example 1B with the following exception: The neutralization process is stopped after the mixture of acid mix and $NaOCH_3$/methanol solution reaches a pH value of 11.2. The purpose for this is to determine the effect an alkaline pH would have on the DMS level in the context of a reverse batch neutralization. About 415 grams of acid mix is required for this neutralization to be complete (to a pH of 11.2). 560 ml of the $NaOCH_3$/methanol solution described in 1B is used.

Sample 1D—Batch reaction; acid into base. Sample 1D comprises a methanol digested, sulfonated methyl ester acid mix. This sample is subjected to an additional process step (as compared to the acid mixes in Samples 1A, 1B, 1C and 1E) prior to neutralization. Methanol is added to the acid mix in a methanol digestion process step, i.e., reacted with 10% methanol as described above. The methanol digested acid mix is neutralized in a reverse batch neutralization step described in Sample 1B using the $NaOCH_3$/methanol solution described in 1B. About 455 grams of acid mix is required for the neutralization to be complete (to a pH of 7.3). Finally, an additional 19–20 grams of the $NaOCH_3$/methanol solution is added to achieve a pH of 9.5.

Sample 1E—Continuous neutralization. Sample 1E is neutralized via a continuous neutralization process step wherein the acid mix is neutralized with a 25% $NaOCH_3$/methanol solution in which the acid and base are introduced simultaneously into the reaction vessel. This process is termed "continuous" neutralization. Two separate pumps are calibrated to deliver precise amounts of acid mix and $NaOCH_3$/methanol solution necessary to maintain a neutral pH in a 4 liter reaction vessel. The process is conducted under high shear continuous mixing. Each pump simultaneously pumps acid mix or $NaOCH_3$/methanol solution into the reaction vessel comprising a high shear mixer (Ross model ME100) operating at 300–400 rpm and these reactants are allowed to react in the vessel and no product is removed. The flow rates for the acid mix and $NaOCH_3$/methanol solution are adjusted to about equi-molar rates. The total flow rate of the acid mix and $NaOCH_3$/methanol solution combined is between about 25–30 ml per minute. The temperature is maintained at about 130° F. (54.4° C.). The pH of the mixture is monitored frequently and is maintained between 7 and 8 during the run which lasts about 57 minutes.

Samples 1A–1E are tested for dimethyl sulfate (DMS) according to the following qualitative method using a Drager Detection Tube (Part No. 6718701) as the detector:

A 10 gram sample of neutralized solution is placed into a 500 ml Erlenmeyer flask along with 25 ml of highly refined white mineral oil. The flask is fitted with a 2 hole stopper. One hole is fitted with a hollow glass tube to the atmosphere; the second hole is also fitted with a hollow glass tube to which is attached a short piece of inert, flexible tubing. The flexible tubing is connected to the inlet side of a Drager air sample/DMS detection tube. The outlet side of the Drager tube is connected with flexible hose to a small air sampling pump calibrated to pump one liter of air per minute. The flask is placed into a constant temperature bath maintained at 60° C. and is agitated continuously while the pump is started and the headspace air-sweep procedure is conducted. Samples are subjected to the headspace air-sweeping procedure for ten minutes. After the air sweeping procedure is completed, the Drager tube color is developed and evaluated for the presence of DMS, and the correlating Qualitative result assigned according to the following Table:

| Drager tube readings | Qualitative results |
|---|---|
| <0.005 | Negative |
| 0.005 | Positive |
| 0.01 | Positive |
| 0.02 | Positive |
| 0.05 | Positive |

The Samples are also tested for disalt impurity and unreacted fatty acid methyl ester. The results for each Samples are in Table 1.

TABLE I

| Sample | DMS | disalt, % by weight | fatty acid methyl ester, % by weight |
|---|---|---|---|
| 1A | positive | 11.3 | 4.0 |
| 1B | negative | 27.8 | 4.9 |
| 1C | negative | 41.8 | 4.4 |
| 1D | negative | 31.5 | 4.3 |
| 1E | negative | 10.8 | 1.3 |

The results show that the continuous neutralization step utilized for Sample 1E provides lower impurity levels and a negative DMS reading. Although Samples 1B–1D provide negative DMS readings, the neutralization methods result in unacceptable levels of impurities. Sample 1A provides lower impurity levels, but gives a positive DMS reading. Sample 1E also provides the lowest level of unreacted methyl ester.

EXAMPLE II

The acid mix comprising the acid form of sulfonated fatty acid methyl esters is prepared by following the process in Example I using the same methyl ester starting material.

Several samples of the sulfonated methyl ester acid mix are then reacted with methanol according to the following methanol digestion step:

The methanol digestion step consists of a recirculating loop with a gear pump and heat exchanger. Methanol is metered into the loop just before a motionless mixer, then into the heat exchanger where the heat of reaction is removed. The loop is forwarded to a jacketed plug flow reactor where the reaction is completed via digestion. The temperature in the loop and the digester is 85° C., and the residence times in the loop and digester are 6.5 and 24 minutes, respectively. The amount of methanol is varied according to the experimental plan from 0% to 20% by weight of the feed add (See Table 2).

The samples of methanol digested add mixes are then subjected to a neutralization process step as follows:

The neutralization is performed continuously (FIG. 1). Individual samples of the methanol digested acid mix (3) and $NaOCH_3$/methanol (5) solutions (varying in concentration) are simultaneously metered directly into the mixing zone of a high shear Ross mixer (1) in a 1000 ml narrow profile Pyrex beaker (4). The beaker is in a constant temperature bath to maintain the temperature inside the beaker at the desired setpoint. The feeds (3), (5) are added with two Cole-Parmer computer controlled peristaltic pumps. The feed rates for the acid mix (3) and $NaOCH_3$/methanol (5) solution range from about 33 to 40 ml/min and about 25 to 70 ml/min, respectively. A piece of Parafilm is placed over the top of the beaker (4) to reduce evaporation losses. A dip tube connected to another Cole-Parmer peristaltic pump is used to withdraw the neutralized product (2) thereby controlling the level of the reactants in the beaker (4) during continuous neutralization. [See below for an illustration of neutralization apparatus.]

During operation, the acid mix flow is set to the desired setpoint, then a predetermined concentration of sodium methoxide/methanol solution is metered into the mixer to control the pH at a target pH of the mixture in the reaction vessel between 3 and 11. The temperature in the constant temperature bath is adjusted for each condition to achieve the desired temperature in the beaker, measured by a hand held thermocouple display unit. After the desired set points have been achieved, the unit is run for a time period long enough to turn over the contents of the beaker four times (98% steady state).

The process described above is conducted on several samples of the acid mix in accordance with the levels of methanol (during the methanol digestion step), the concentrations and levels of $NaOCH_3$/methanol solution (during the neutralization step), and the temperatures and pH (during the neutralization step) as set forth in Table 2. The Samples are analyzed for sulfonated fatty acid methyl ester content and impurity (disalt, soaps, and methyl ester) content. See Table 2. The Samples are also quantitatively analyzed for dimethyl sulfate (DMS) content. See Table 3.

TABLE 2

| Sample | Methanol[1] | $NaOCH_3$ conc.[2] | $NaOCH_3$/$CH_3OH$[3] | Temp[4] | pH[5] | total methanol[6] | MES Yield[7] | MES[8] | disalt[9] | ME[10] | soap[11] |
|---|---|---|---|---|---|---|---|---|---|---|---|
| 1 | 10.0 | 14.7 | 1.13 | 50.5 | 6.7 | 49.1 | 95.42 | 95.77 | 3.00 | 0.82 | 0.40 |
| 2 | 10.0 | 9.5 | 1.74 | 51.7 | 10.3 | 57.4 | 95.84 | 96.17 | 2.74 | 0.63 | 0.45 |
| 3 | 10.0 | 14.7 | 1.13 | 60.3 | 6.6 | 46.0 | 95.71 | 96.09 | 2.70 | 0.78 | 0.44 |
| 4 | 10.0 | 14.7 | 1.13 | 42.5 | 6.8 | 48.6 | 95.27 | 95.69 | 2.97 | 0.87 | 0.47 |
| 5 | 20.0 | 10.1 | 1.51 | 59.0 | 6.6 | 57.0 | 96.16 | 96.54 | 2.29 | 0.70 | 0.48 |
| 6 | 20.0 | 25.5 | 0.60 | 41.6 | 6.1 | 37.3 | 95.63 | 96.00 | 2.80 | 0.68 | 0.52 |
| 7 | 20.0 | 25.5 | 0.60 | 56.6 | 10.3 | 35.6 | 96.42 | 96.81 | 2.01 | 0.69 | 0.50 |
| 8 | 20.0 | 13.1 | 1.16 | 40.1 | 10.2 | 50.9 | 96.19 | 96.56 | 2.28 | 0.66 | 0.50 |
| 9 | 20.0 | 16.0 | 0.95 | 52.0 | 3.8 | 47.8 | 95.11 | 95.55 | 3.05 | 0.83 | 0.57 |
| 10 | 14.4 | 9.8 | 1.63 | 40.0 | 4.0 | 59.9 | 94.91 | 95.32 | 3.33 | 0.80 | 0.56 |
| 11 | 5.6 | 21.2 | 0.82 | 42.5 | 10.6 | 38.8 | 93.99 | 94.37 | 4.27 | 0.90 | 0.46 |
| 12 | 0.0 | 10.1 | 2.01 | 54.4 | 5.2 | 59.1 | 82.77 | 82.93 | 15.65 | 0.79 | 0.63 |
| 13 | 0.0 | 18.0 | 1.14 | 44.1 | 3.5 | 39.0 | 82.64 | 82.73 | 16.09 | 0.61 | 0.57 |
| 14 | 0.0 | 15.2 | 1.34 | 62.0 | 7.4 | 48.1 | 81.83 | 81.91 | 16.89 | 0.77 | 0.43 |
| 15 | 0.0 | 22.2 | 0.92 | 61.0 | 6.7 | 31.1 | 84.48 | 84.61 | 14.17 | 0.82 | 0.39 |
| 16 | 0.0 | 10.1 | 2.01 | 42.1 | 7.2 | 60.5 | 83.54 | 83.67 | 15.10 | 0.73 | 0.51 |
| 17 | 10.0 | 14.7 | 1.13 | 50.5 | 6.7 | 47.4 | 96.38 | 96.73 | 2.18 | 0.71 | 0.38 |
| 18 | 10.0 | 22.3 | 0.74 | 60.0 | 3.4 | 31.2 | 95.57 | 95.92 | 2.91 | 0.65 | 0.51 |
| 19 | 10.0 | 14.7 | 1.13 | 50.5 | 6.7 | 45.6 | 94.81 | 95.20 | 3.49 | 0.89 | 0.42 |

[1]% by weight, methanol used in methanol digestion step.
[2]% by weight, concentration of $NaOCH_3$ in methanol used in neutralization step.
[3]grams $NaOCH_3$/methanol solution per gram of acid mix in neutralization step.
[4]°C., temperature achieved in neutralization step.
[5]actual pH of solution in the neutralization step measured from a 1–2%, by weight to the surfactant, solution in deionized water with a pH meter.

TABLE 2-continued

| Sample | Methanol[1] | NaOCH$_3$ conc.[2] | NaOCH$_3$/ CH$_3$OH[3] | Temp[4] | pH[5] | total methanol[6] | MES Yield[7] | MES[8] | disalt[9] | ME[10] | soap[11] |
|---|---|---|---|---|---|---|---|---|---|---|---|

[6]% by weight, total methanol in solution during neutralization step, as measured experimentally.
[7]molar percentage of methyl ester feedstock converted to sulfonated fatty acid methyl ester.
[8]% by weight of the surfactant, sulfonated fatty acid methyl esterd in the surfactant.
[9]% by weight of the surfactant, sulfonated fatty acid methyl ester disalt impurity in the surfactant.
[10]% by weight of the surfactant, fatty acid methyl ester impurity in the surfactant.
[11]% by weight of the surfactant, fatty acid salt (soap) impurity in the surfactant.

TABLE 3

| Sample | Age Time (minutes) | DMS Tube Grade | DMS ppm[1] |
|---|---|---|---|
| 1 | 5 | 1 | 0.066 |
|   | 18 | 0 | 0.044 |
|   | 62 | 0 | 0.044 |
| 2 | 5 | 1 | 0.070 |
|   | 18 | 0 | 0.047 |
|   | 62 | 0 | 0.047 |
| 3 | 5 | 4 | 0.574 |
|   | 18 | 4 | 0.574 |
|   | 62 | 0 | 0.038 |
| 4 | 5 | 1 | 0.061 |
|   | 18 | 0 | 0.041 |
|   | 62 | 0 | 0.041 |
| 5 | 5 | 2 | 0.128 |
|   | 18 | 0 | 0.047 |
|   | 62 | 0 | 0.047 |
| 6 | 5 | 0 | 0.037 |
|   | 18 | 0 | 0.037 |
|   | 62 | 0 | 0.037 |
| 7 | 5 | 0 | 0.033 |
|   | 18 | 0 | 0.033 |
|   | 62 | 0 | 0.033 |
| 8 | 5 | 4 | 0.678 |
|   | 18 | 2 | 0.124 |
|   | 62 | 1.5 | 0.068 |
| 9 | 5 | 0 | 0.046 |
|   | 18 | 0 | 0.046 |
|   | 62 | 0 | 0.046 |
| 10 | 5 | 0 | 0.055 |
|   | 18 | 0 | 0.055 |
|   | 62 | 0 | 0.055 |
| 11 | 5 | 0 | 0.040 |
|   | 18 | 0 | 0.040 |
|   | 62 | 0 | 0.040 |
| 12 | 5 | 0 | 0.065 |
|   | 18 | 0 | 0.065 |
|   | 62 | 0 | 0.065 |
| 13 | 5 | 0 | 0.044 |
|   | 18 | 0 | 0.044 |
|   | 62 | 0 | 0.044 |
| 14 | 5 | 2 | 0.151 |
|   | 18 | 0 | 0.055 |
|   | 62 | 0 | 0.055 |
| 15 | 5 | 1 | 0.040 |
|   | 18 | 0 | 0.040 |
|   | 62 | 0 | 0.040 |
| 16 | 5 | 2 | 0.184 |
|   | 16 | 0 | 0.067 |
|   | 62 | 0 | 0.067 |
| 17 | 5 | 2 | 0.106 |
|   | 18 | 0.5 | 0.039 |
|   | 62 | 0 | 0.039 |
| 18 | 5 | 0 | 0.034 |
|   | 18 | 0 | 0.034 |
|   | 62 | 0 | 0.034 |
| 19 | 5 | 2 | 0.122 |
|   | 18 | 1 | 0.066 |
|   | 62 | 0.5 | 0.044 |

[1]parts DMS per million parts sulfonated fatty acid methyl ester in the surfactant.

The quantitative method for determination of DMS generally follows the qualitative method set forth in Example I:

Ten gram Samples of neutralized acid mix are taken, promptly weighed into the 25 grams of mineral oil and held at the temperature employed for neutralizing the sample prior to this determination. Samples are measured for DMS at the following hold times: 5 min., 18 min. and 62 min.

Quantitative measurements are made possible by a spike/recovery experiment. Known quantities of DMS are spiked into the oil and recovered by the Drager Tube procedure by passing vapor through the tubes as well as by directly injecting similar known quantities of DMS into another set of Drager Tubes. Results of this experiment are shown below:

| | Drager Tube Reading Avg. (Drager) | |
|---|---|---|
| Micrograms DMS Added | Direct Injection Into Tube | Purged From Spiked Mineral Oil |
| 0.00 | "no color" | "no color" |
| 0.30 | 0.005 | 0.095 |
| 0.60 | 0.012 | 0.012 |
| 0.90 | 0.018 | 0.018 |
| 1.20 | 0.020 | 0.020 |
| 3.00 | 0.050 | 0.050 |

Since the numbers engraved on the Drager Tubes apply to ppm quantities in air, and since the quantities of DMS are desired on a ppm basis of the active surfactant, the Drager Tube Readings have been modified to the scale shown in the following table which is used for the study reported in Table 3.

| Micrograms DMS | Drager Tube Reading (Drager) | Tube Grade Assigned |
|---|---|---|
| 0.20* | "no color" | 0 |
| 0.30 | 0.005 | 1 |
| 0.55 | 0.010 | 2 |
| 1.20 | 0.020 | 3 |
| 3.00 | 0.050 | 4 |

*0.2 micrograms DMS is used as conservative estimate of DMS found in samples with a "0" Tube Grade.

Using the Tube Grade column for assignment of color developed in the Drager Tubes, and correlating with the micrograms DMS from the above chart, quantitative DMS readings are assigned to all samples by taking the micrograms DMS and dividing by the analytical result for methyl ester sulfonate in the 10 gram sample.

In the case where no discernible color is produced in the Drager Tube (Tube Grade 0), although the DMS is below the detection limit, a conservative estimate of 0.20 micrograms DMS is assigned to those samples for calculation of ppm DMS on the basis of methyl ester sulfonate content. Since DMS Tube Grade generally decreases with sample age time (for those samples with positive Tube Grade readings), testing is generally terminated once a Tube Grade of 0 has been reached, and the estimate of 0.2 micrograms DMS is assigned to these samples and subsequent samples in that time series.

Samples 1-11 and 17-19 fall within the scope of the process of the invention herein. These sulfonated fatty acid methyl ester surfactant pastes exhibit high yield and purity and can be used in detergent compositions following a working-up process including, e.g., separating the surfactant from the methanol and color-body impurities. These pastes also exhibit good in-process flow properties. Samples 12-16 are comparative samples. These samples are not subjected to a separate methanol digestion step which results in surfactant mixtures containing undesirable levels of impurities, particularly a high level of disalt impurity. One important learning made from this data is that Samples 12-16 did not provide high purity product even though there is excess methanol present in the neutralization process step; a separate methanol digestion step is required to provide the benefits herein.

EXAMPLE III

The acid mix comprising the acid form of sulfonated fatty acid methyl esters is prepared by following the process in Example I using the same methyl ester starting material.

The digested acid mix is then reacted with methanol according to the following methanol digestion step:

The acid mix is reacted with 16% methanol, by weight of the acid mix. The reaction is conducted for 40–50 minutes at a temperature of approximately 80° C. in a closed vessel, in-line following the sulfonation step.

Figure 2:
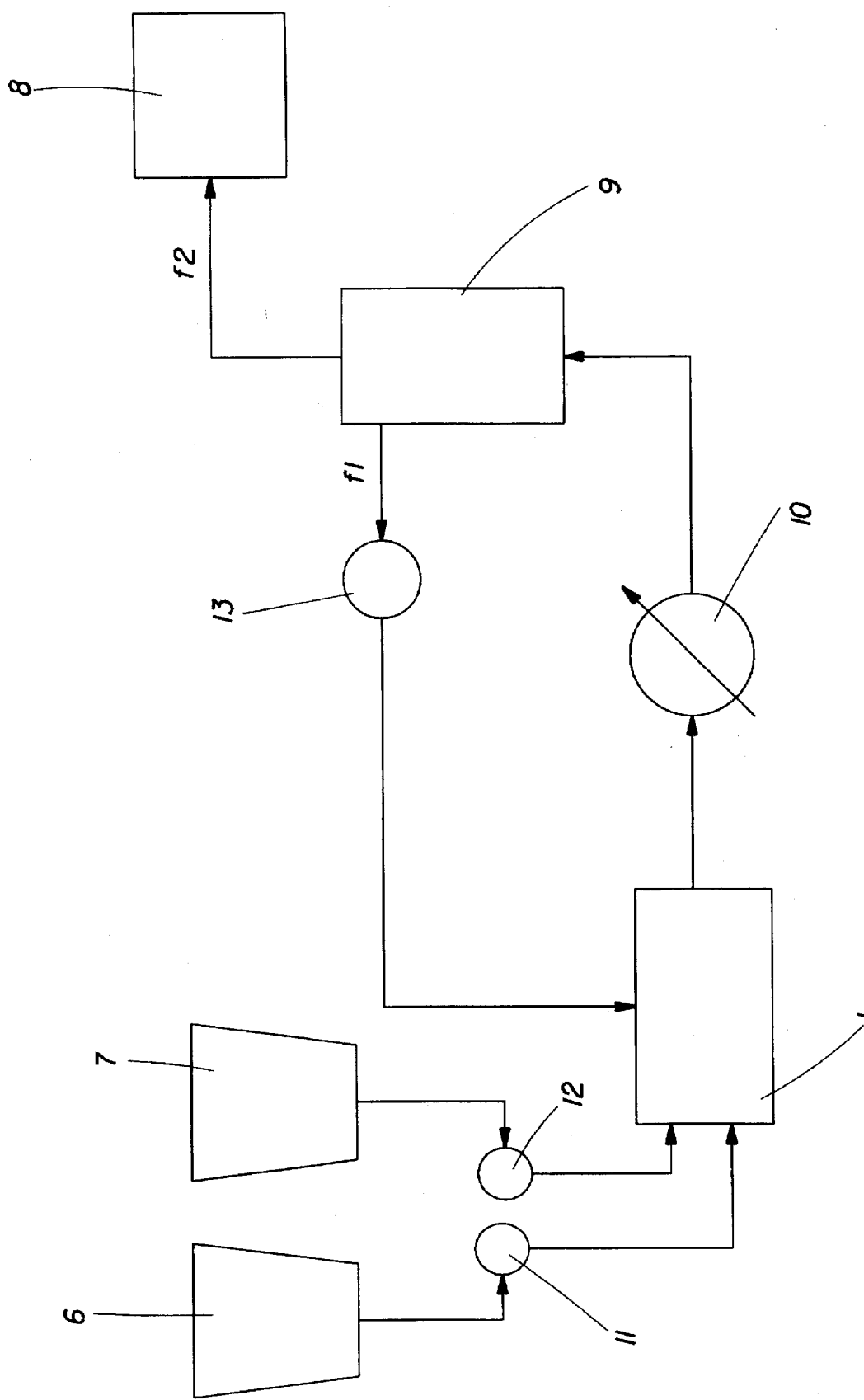

The methanol/acid mix is then neutralized in a continuous, closed loop, dominant bath system (FIG. 2). The neutralization process comprises continuously neutralizing the methanol/acid mix (6) with a NaOCH$_3$/methanol solution (7) at 16.7% w/w concentration. The closed loop, dominant bath system comprises a heat exchanger (10), a holding tank (9), and a recycle pump (13). [The neutralization process is conducted in a continuous, closed loop, dominant bath system. See below.] The recycle ratio, defined as the amount recycled neutralized product (f1) to the amount removed from the loop (f2), is 15–20 to 1. The average residence time in the neutralizing loop is 15–20 minutes. The acid mix (6) and base (7) are pumped simultaneously into the shear zone of a high shear driven mixer (Ross model ME 400 L at 10,000 rpm) (1) and at precise proportions so as to maintain an essentially neutral pH of 6 to 8 in the finished product.

The feed rate for the methanol/acid (6) is 500–550 gms per minute. The feed rate for sodium methoxide/methanol solution (7) is 400–450 gms per minute. Each component is pumped in dedicated lines, using dedicated pumps (11) (12). The temperature of the neutralization step is maintained at 60°–65° C. The target level of total alcohol in the finished product is 50%.

The finished product (surfactant paste with methanol) is analyzed for sulfonated methyl esters, and impurities, and is stored in a storage tank (8). The results appear in Table 4.

TABLE 4

|  | % by weight of the acid mix | % by weight of Analyzed Components |
|---|---|---|
| Acid mix Feed into neutralization loop | | |
| HMES[1] | 69.3 | 92.4 |
| DiAcid & fatty acid | 3.0 | 4.0 |

TABLE 4-continued

|  | % by weight of the acid mix | % by weight of Analyzed Components |
|---|---|---|
| PEE[2] | 2.7 | 3.6 |
| Finished Neutralized Product | | |
| MES[3] | 43.2 | 93.2 |
| DiSalt & Soap impurities | 2.4 | 5.2 |
| PEE[2] | 0.7 | 1.6 |
| MeOH | 37.2 | — |
| KF Moisture | 4.8 | — |
| Na$_2$SO$_4$ | 0.7 | — |
| NaCH$_3$SO$_4$ | 3.8 | — |

[1] Acid form of sulfonated fatty acid methyl esters
[2] Petroleum Ether Extract
[3] Sulfonated fatty acid methyl ester salts The resultant product contains a high-purity sulfonated fatty acid methyl ester surfactant and exhibits good in-process flow properties.

The neutralized solution comprising the surfactant and methanol may then be diluted with additional methanol or be concentrated to achieve an overall solids content of 20 to 50% or higher as desired for final work-up and recovery of the surfactant.

This mixture is heated to between 45° and 75° C. and filtered through a Mott sintered metal filtration apparatus to remove gross insoluble solids. The pore size in the filter can be from 5 to 20 microns. This step is referred to as a filtration step. It is followed by a process step for color body removal via purification with activated carbon. The Mott filter system temperature is maintained at 45° to 75° C. Commercially available filter aid materials (such as diatomaceous earth or powderized cellulose) can be used to improve the efficiency of this step, and can be used as filter pre-coating, as body filter aid, or a combination of pre-coat and body filter aid.

Following the Mott filtration step, the solution of surfactant, impurities (including dark colored impurities) and methanol is then further processed by pumping the solution through columns packed with granular, activated carbon. The concentration of solids in the feed solution to the carbon columns can range from about 15 to 40%. The operating temperature in this step is maintained at about 70° to 85° C. The process is maintained under an operating pressure of about 50 to 70 psig.

This color improved solution is then treated to remove the methanol by evaporation. Afterwards, the recovered purified surfactant is ground into a powder. The purity of this dried powder is, by weight of the powder, 92.3% sulfonated fatty acid methyl esters and 1.8% disalt and soap impurities. Thus the ratio of sulfonated methyl ester to disalt and soap is 51:1. The remainder are impurities primarily consisting of sodium methyl sulfate and water. This illustrates the desirability of the post-neutralization filtration and carbon purification process steps which selectively remove the undesirable disalt impurity from the neutralized acid mix as well as removing the color bodies.

EXAMPLE IV

A magnesium methyl ester surfactant is prepared following the process described in Example III using a Mg(OCH$_3$)$_2$/methanol solution during the neutralization step. The resultant product contains a high-purity sulfonated fatty acid methyl ester surfactant and exhibits good in-process flow properties.

What is claimed is:

1. A no-bleach process for preparing a sulfonated fatty acid alkyl ester surfactant comprising, by weight of the surfactant, from about 90% to 100% of sulfonated fatty acid alkyl esters and less than about 10% of impurities selected from the group consisting of sulfonated fatty acid salts, fatty acid salts, fatty acid alkyl esters, and mixtures thereof; said process comprising the steps of:

a) sulfonating fatty acid alkyl esters;
   b) reacting the product of step a) with about 10% to about 20%, by weight of the product of step a), of a substantially anhydrous $C_1$ to $C_8$ alcohol;
   c) continuously neutralizing the product of step b) with an alkoxide of the formula $(R_2O^-)_n M^{n+}$ having a concentration of from about 5% to 35% by weight, in a substantially anhydrous medium of a $C_1$ to $C_8$ alcohol; wherein $R_2$ is on the average a $C_1$ to $C_8$ alkyl, M is an alkali metal or alkaline earth metal cation, or a mixture thereof, and n is 1 when M is an alkali metal cation and n is 2 when M is an alkaline earth metal cation;
   d) filtering the product of step c); and
   e) purifying the product of step d) in a column of activated carbon;

wherein the total amount of alcohol in step c) is from about 30% to 65% by weight, the temperature during step c) is from about 30° to 70° C. and the pH during step c) is from about 3 to 11; and wherein the process does not consist of a bleaching step.

2. The process of claim 1 wherein the alcohol in step b) comprises a $C_1$ to $C_6$ alcohol.

3. The process of claim 1 wherein the alcohol in step b) is methanol.

4. The process of claim 1 wherein step c) comprises continuously neutralizing the product of step b) with the alkoxide having a concentration of from about 10% to 25% in a substantially anhydrous medium of a $C_1$ to $C_8$ alcohol.

5. The process of claim 3 wherein step c) comprises continuously neutralizing the product of step b) with the alkoxide having a concentration of from about 10% to 25% in a substantially anhydrous medium of methanol.

6. The process of claim 1 wherein the total amount of alcohol in step c) is from about 30% to 40%.

7. The process of claim 3 wherein the total amount of alcohol in step c) is from about 30% to 40%.

8. The process of claim 5 wherein the total amount of alcohol in step c) is from about 30% to 40%.

9. The process of claim 1 wherein the temperature during the neutralizing step c) is from about 40° to 60° C.

10. The process of claim 3 wherein the temperature during the neutralizing step c) is from about 40° to 60° C.

11. The process of claim 5 wherein the temperature during the neutralizing step c) is from about 40° to 60° C.

12. The process of claim 8 wherein the temperature during the neutralizing step c) is from about 40° to 60° C.

13. The process of claim 1 wherein the pH during the neutralizing step c) is from about 6 to about 8.

14. The process of claim 3 wherein the pH during the neutralizing step c) is from about 6 to about 8.

15. The process of claim 5 wherein the pH during the neutralizing step c) is from about 6 to about 8.

16. The process of claim 8 wherein the pH during the neutralizing step c) is from about 6 to about 8.

17. The process of claim 12 wherein the pH during the neutralizing step c) is from about 6 to about 8.

18. The process of claim 1 for preparing the sulfonated fatty acid alkyl ester surfactant of claim 1 wherein the sulfonated fatty acid alkyl esters are of the formula:

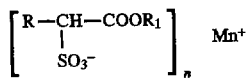

wherein R is on the average a $C_{10}$ to $C_{16}$ alkyl, $R_1$ is on the average a $C_1$ to $C_6$ alkyl, and M is selected from the group consisting of sodium, lithium, potassium, calcium, magnesium, and mixtures thereof; said process comprising:

a) sulfonating fatty acid alkyl esters of the formula $RCH_2COOR_1$ wherein R and $R_1$ are the same as defined above;
   b) reacting the product of step b) with about 10% to 20%, by weight of the product of step a), of a $C_1$ to $C_6$ alcohol; and
   c) continuously neutralizing the product of step b) with the alkoxide having a concentration of from about 10% to 25%, by weight, in a substantially anhydrous medium of a $C_1$ to $C_6$ alcohol; wherein $R_2$ is on the average a $C_1$ to $C_6$ alkyl and M is the same as defined above.

19. A no-bleach process for preparing a sulfonated fatty acid methyl ester surfactant comprising, by weight of the surfactant, from about 90% to 100% of sulfonated fatty acid methyl esters and less than about 10% of impurities selected from the group consisting of sulfonated fatty acid salts, fatty acid salts, fatty acid methyl esters, and mixtures thereof; said process comprising the steps of:

a) sulfonating fatty acid methyl esters;
   b) reacting the product of step a) with about 5% to about 25%, by weight of the product of step a), of a substantially anhydrous $C_1$ to $C_6$ alcohol;
   c) continuously neutralizing the product of step b) with an alkoxide of the formula $(R_2O^-)_n M^{n+}$ having a concentration of from about 5% to 35% by weight, in a substantially anhydrous medium of a $C_1$ to $C_6$ alcohol; wherein $R_2$ is on the average a $C_1$ to $C_8$ alkyl, M is an alkali metal cation or alkaline earth metal cation, or a mixture thereof and n is 1 when M is an alkali metal cation and n is 2 when M is an alkaline earth metal cation;
   d) filtering the product of step c); and
   e) purifying the product of step d) in a column of activated carbon;

wherein the total amount of alcohol in step c) is from about 30% to 65% by weight, the temperature during step c) is from about 30° to 70° C. and the pH during step c) is from about 5 to 9; and wherein the process does not consist of a bleaching step.

20. The process of claim 18 wherein the alcohol in step b) is methanol, the alkoxide in Step c) is $(CH_3O^-)_n M^{n+}$, and the alcohol in step c) is methanol.

21. The process of claim 20 wherein the concentration of methoxide in methanol is from about 10% to 25% by weight and the total amount of methanol in step c) is from about 30% to 40%.

22. The process of claim 20 wherein the temperature is from about 40° to 60° C.

23. The process of claim 21 wherein the temperature is from about 40° to 60° C.

24. The process of claim 20 wherein the pH is from about 6 to 8.

25. The process of claim 21 wherein the pH is from about 6 to 8.

26. The process of claim 22 wherein the pH is from about 6 to 8.

* * * * *